United States Patent [19]
Beretta

[11] Patent Number: 6,042,831
[45] Date of Patent: Mar. 28, 2000

[54] HUMAN IMMUNODEFICIENCY VIRUS TYPE 1 (HIV-1) GP160 EPITOPES THAT ARE IMMUNOLOGICALLY HOMOLOGOUS TO EPITOPES LOCATED IN THE CLASS I MAJOR HISTOCOMPATIBILITY COMPLEX (MHC) HEAVY CHAIN α-1 DOMAIN

[75] Inventor: Alberto Beretta, Milan, Italy

[73] Assignee: La Fondation Mondiale Recherche et Prevention Sida, Cedex

[21] Appl. No.: 08/335,733

[22] PCT Filed: May 10, 1993

[86] PCT No.: PCT/IT93/00049

§ 371 Date: Nov. 10, 1994

§ 102(e) Date: Nov. 10, 1994

[87] PCT Pub. No.: WO93/23427

PCT Pub. Date: Nov. 25, 1993

[30] Foreign Application Priority Data

May 11, 1992 [IT] Italy ................................. RM92A0350

[51] Int. Cl.[7] .................................................. A61K 39/21
[52] U.S. Cl. ..................................... 424/188.1; 424/208.1; 530/327; 530/328; 530/300
[58] Field of Search ........................... 530/300, 324–326, 530/350; 424/184.1–188.1, 207.1, 208.1

[56] References Cited

U.S. PATENT DOCUMENTS 4,943,628  7/1990  Rosen et al. ............................ 530/326

FOREIGN PATENT DOCUMENTS

WO 9205196  4/1992  WIPO .
WO 9205800  4/1992  WIPO .
WO 9323427  11/1993  WIPO .

OTHER PUBLICATIONS

Grassi et al., 1991, "Human immunodeficiency virus type 1 gp120 mimics a hidden monomorphic epitope borne by class I major histocompatibility complex heavy chains", J. Exp. Med. 174:53–62.
Nara et al., 1991, "Neutralization of HIV–1: a paradox of humoral proportions", FASEB J. 5:2437–2455.
Brolidan et al., 1992, "Identification of human neutralization–inducing regions of the human immunodeficiency virus type 1 envelope glycoproteins", Proc. Natl. Acad. Sci. USA 89:461–465.
Harlow et al., "Immunizations", in Antibodies: A Laboratory Manual, Harlow et al., eds., Cold Spring Harbor Laboratory, pp. 92–94 and 100–102, 1988.
Graham et al., 1995, New Engl. J. Med. 333:1331–1339.
Haynes, 1993, Science 260:1279–1286.
Stein et al., 1993, Clin. Infect. Dis. 17:749–771.
Beretta et al. (1987) Eur. J. Immunol. 17:1793.
Nick et al. (1991) AIDS Forschung 6:467.
Palker et al. (1989) J. Immunol. 142:3612.
"Cross–Reactive Response to Human Immunodeficiency Virus Type 1 (HIV–1) gp120 and HLA Class I Heavy Chains Induced by Receipt of HIV–1–Derived Envelope Vaccines" by De Santis et al.; Journal of Infectious Diseases 1993, pp. 1396–1403.
"Preferential Vβ Usage by Cytotoxic T Cells Cross–Reactive between Two Epitopes of HIV–1 gp160 and Degenerate in Class I MHC Restriction" by Shirai et al. The Journal of Immunology, vol. 151, pp. 2283–2295, No. 4, Aug. 15, 1993.
"Identification of human neutralization–inducing regions of the human immunodeficiency virus type 1 envelope glycoproteins" by Broliden et al. Proc. Natl. Acad. Sci. USA; Immunology, vol. 89, pp. 461–465, Jan. 1992.
"Fine Specificity of the Murine Antibody Response to HIV–1 gp160 Determined by Synthetic Peptides which Define Selected Epitopes" by Wolf et al., Molecular Immunology, vol. 29, No. 7/8, pp. 989–998, 1992.
"Human Immunodeficiency Virus Type 1 gp120 Mimics a Hidden Monomorphic Epitope Borne by Class I Major Histocompatibility Complex Heavy Chains" by Grassi et al. J. Exp. Med. 174, pp. 52–62, 1992.
"Neutralization of HIV–1: a paradox of humoral proportions" by Nara et al., The FASEB Journal, vol. 5, Jul. 1991; pp. 2437–2455.
Contents The Journal of Experimental Medicine, vol. 170, No. 6, Dec. 1, 1989, pp. 2022–2035; "Structural Requirements for Class I MHC Molecule–Mediated Antigen Presentation and Cytotoxic T Cell Recognition of an Immunodominant Determinant of the Human Immunodeficiency Virus Envelope Protein" by Takahashi et al.
"AIDS Forchung" by Nick et al., 1991 6: 46; pp. 467–473.
Palker et al., 1989, J. Immunol. 142: pp. 3612–3619.
Beretta et al., 1987, Eur. J. Immunol. 17: pp. 1793–1798.

*Primary Examiner*—Laurie Scheiner
*Assistant Examiner*—Jeffrey S. Parkin
*Attorney, Agent, or Firm*—Ronald B. Hildreth; Baker & Botts, LLP

[57] ABSTRACT

This invention is directed toward human immunodeficiency virus type 1 (HIV-1) peptidic epitopes derived from the envelope glycoprotein gp160 which are immunologically homologous to epitopes located in the class I major histocompatibility complex (MHC) heavy chain α-1 domain. These peptides should prove useful in the preparation of immunodiagnostic reagents.

8 Claims, 8 Drawing Sheets

HUMAN IMMUNODEFICIENCY VIRUS TYPE 1 (HIV-1) GP160 EPITOPES THAT ARE IMMUNOLOGICALLY HOMOLOGOUS TO EPITOPES LOCATED IN THE CLASS I MAJOR HISTOCOMPATIBILITY COMPLEX (MHC) HEAVY CHAIN α-1 DOMAIN

The invention concerns epitopes of the HIV virus gp160 protein, that are immunologically homologous to epitopes of the protein family of the human major histocompatibilty complex HLA, to be used for diagnosing and immunization.

Among the mechanisms thought to be responsible of AIDS, it has been suggested that auto-immunity, namely auto-antibody induction mechanism, may play a major role (Hebeshaw J. A and Dalgleish A. G., J. Acquired Immun. Defic. Syndrome, 2, 457, 1989). The homology of portions of virus components with endogenous proteins of the human body could reduce the self-tolerance immunity mechanisms, thus causing the synthesis of antibodies, and activating cytotoxic T lymphocytes.

The gp120 protein is used to produce vaccines for immunization of HIV infection, as a complex with the gp41 protein, such complex being defined as gp160 (ref.).

The PCT Application No. WO89/09618 claims anti-HIV vaccines devoided of gp160 fragments generating HIV-1 infection enhancing antibodies. However, the cited application does not disclose any gp160 epitope able to induce auto-antibodies in HIV-infected subjects.

The PCT Application No. WO92/05196 concerns alloepitopes of HIV gp160 recognized by CD4+T cell receptors, having a three-dimensional structure (α-helix) similar to the region of the human Major Hystocompatibiliy Complex (MHC). However, also this cited application does not disclose any gp160 epitope able to induce auto-antibodies in HIV-infected subjects.

The inventor previously isolated and described two monoclonal antibodies, M38 and L31, which react with the HIV virus gp160 protein as well as with the class I HLA protein (Beretta et al., Eur. J. Immunol., 17, 1793–1798, 1987; Grassi et al., J. Exp. Med., 174, 53–62, 1980).

The gene coding said cell protein was idendified and sequenced (Grassi et al., J. Exp. Med., 174, 53–2562, 1980)

Therefore it results obvious the need to identify homology regions between HLA and HIV proteins, either for diagnosis purpose in order to identify crossreactive antibodies in the serum of either AIDS patients or HIV vaccinated subjects, and to produce recombinant vaccines.

In the context of this invention, "epitopes" mean fractions of an antigen molecule that are recognized and/or are able to bind a specific antibody; "immunologically homologous epitopes" mean epitopes of at least two different antigen molecules, that are recognized and/or are able to bind the same antibody; "macromolecular structures" mean either cells, or parts thereof, or proteins, or parts, thereof.

The author has analyzed sequences of both HLA and gp160 proteins, and identified immunologically homologous regions. Further tests with synthetic peptides of the HLA heavy chains have allowed to identify more precisely an immunologically homologous region of gp160 and of the heavy chain of class I HLA. This region corresponds to a specific polypeptide segment of the gp160 protein, wherein two minimum epitope sequences have been defined. The immunologically homologous regions on HLA and the minimum sequence of the epitopes have been identified too.

In the gp 160 protein, said epitopes are separated by a 9 amino acid intervening sequence which is shown not to be immunogenic in the context of the natural gp160 protein, in HIV infected subjects. However, experiments published by Helseth et al. (Journ of Virol. 65, 2119–2123, 1991) showed that 5 of said 9 residues are essential to the maintenance of the quaternary structure of the HIV envelope, since single amino acid substitutions within these positions result in a high dissociation rate between gp120 and gp41. The author of the present invention has also determined that said sequence may be able to induce anti-HIV neutralizing antibodies, when used without its natural flanking sequences.

Therefore an object of this invention are epitopes of the HIV gp160 protein which are immunologically homologous to at least one epitope of the HLA class I heavy chains α-1 domain protein which is comprised in the following sequence:

TQKYKRQAQADRVNLRKLRGYY (SEQ ID NO.2).

According to a preferred embodiment said epitopes are comprised in the region having the following amino acid sequence:

SELYKYKVVKIEPLGVAPTKAKRRVV (SEQ ID NO.1).

Preferably said gp160 region comprises two epitopes, more preferably having the amino acid sequences as follows:

SELYKYKVVK (SEQ ID. NO:3) and PTKAKRRVV (SEQ ID. NO:4).

According to an embodiment of this invention said epitopes are recognized by neutralizing antibodies.

According to a further embodiment of this invention said epitopes are immunologically homologous to a bacterial superantigen, preferably to the SEE protein of *E. coli*.

Always according to the invention said epitopes are of either natural, or recombinant, or synthetic origin.

It is a further object of the invention the use of epitopes as disclosed in the present specification, for the preparation of compositions of immunodiagnostic and for immunization purposes.

Another object of the invention are immunodiagnostic kits, comprising as specific ligand macromolecular structures comprising at least one of the epitopes according to the invention, to detect antibodies from a sample of serum from either AIDS affected or HIV immunized subjects, said antibodies being able to react also with at least one epitope of HLA protein family. Preferably said epitopes comprise comprise the region having the following sequence: IEPLGVAPT (SEQ ID no:5).

Said immunodiagnostic diagnostic kits comprise any of the known binding-detection systems, preferably ELISA, RIA or Western Blot systems.

A further object of this invention are antigenic compositions for HIV vaccines which comprise a sterile carrier and the gp160 protein or parts thereof characterized in either lacking at least one of the epitopes which are immunologically homologous to HLA having the following amino acid sequence SELYKYKVVK (SEQ ID no:3) and PTKAKRRVV (SEQ ID no:4) respectively, or being modified to make at least one of said epitopes not immunologically )homologous to HLA, and in comprising the region having following sequence: IEPLGVAPT (SEQ ID no:5).

It is an object of the invention polyclonal or monoclonal antibodies able to recognize the gp160 region: IEPLGVAPT (SEQ ID no:5) and having a neutralizing activity.

Another object of the invention is the use of said antibodies for the preparation of pharmaceutical compositions for the imuunotherapy of HIV infected subjects The invention will be described in the following, by some explicative but not limitative examples, with reference to the annexed figures, wherein.

Figure 9:
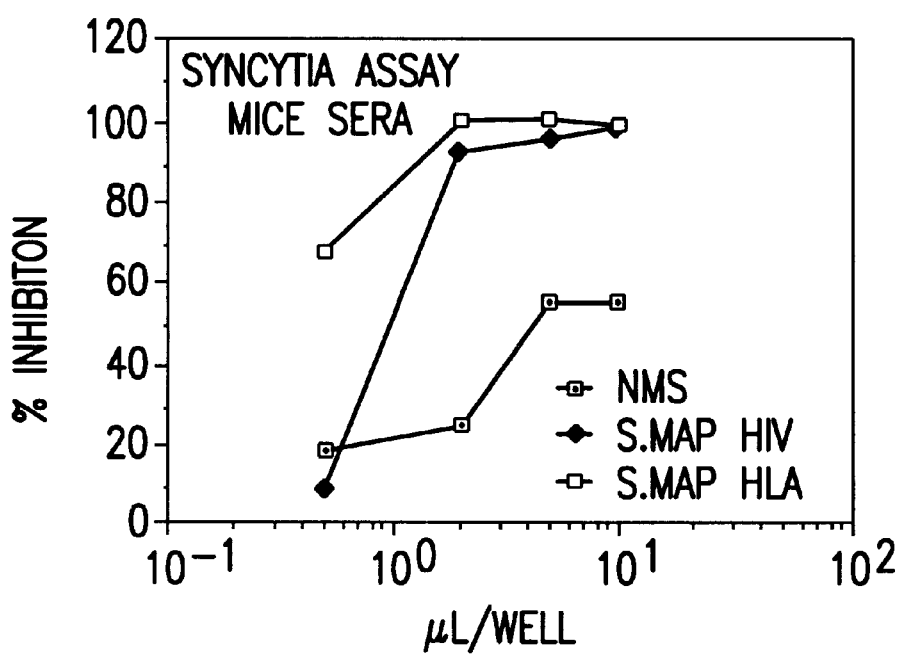
Figure 2A:
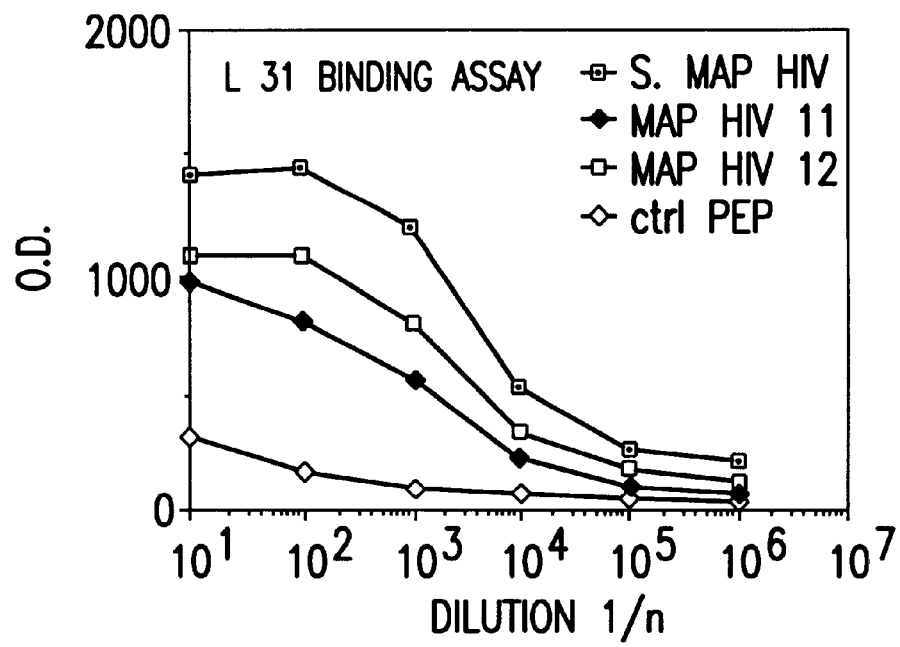
FIG. 2 shows the binding of M38 (panel a and b) and L31 (panel c and d) antibodies to different peptides.
Figure 2B:
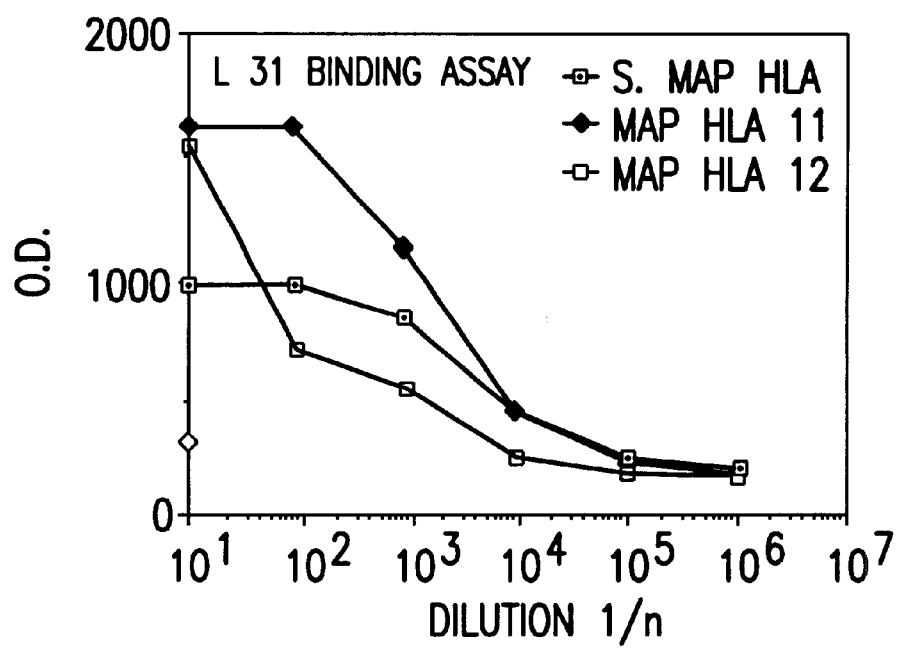
Figure 2C:
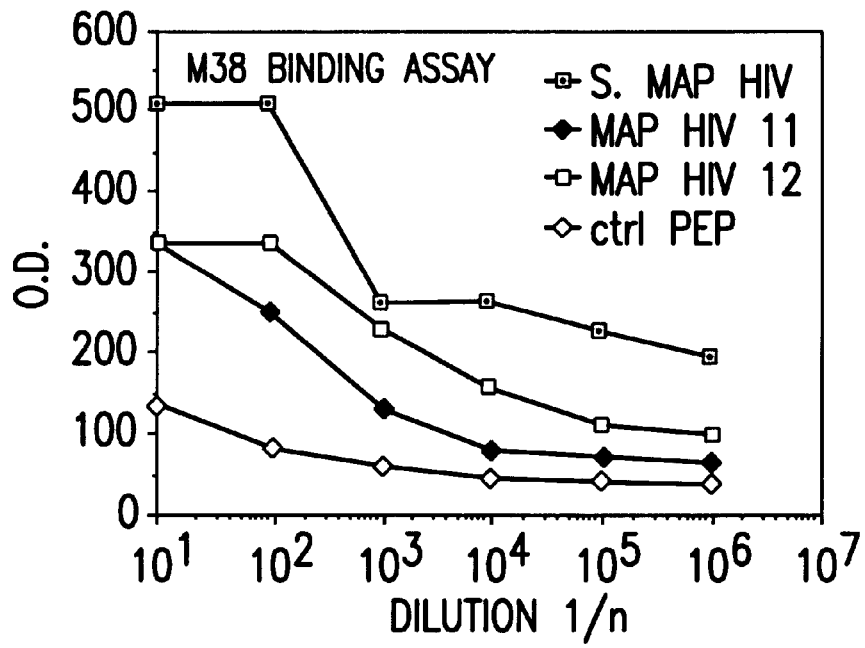
Figure 2D:
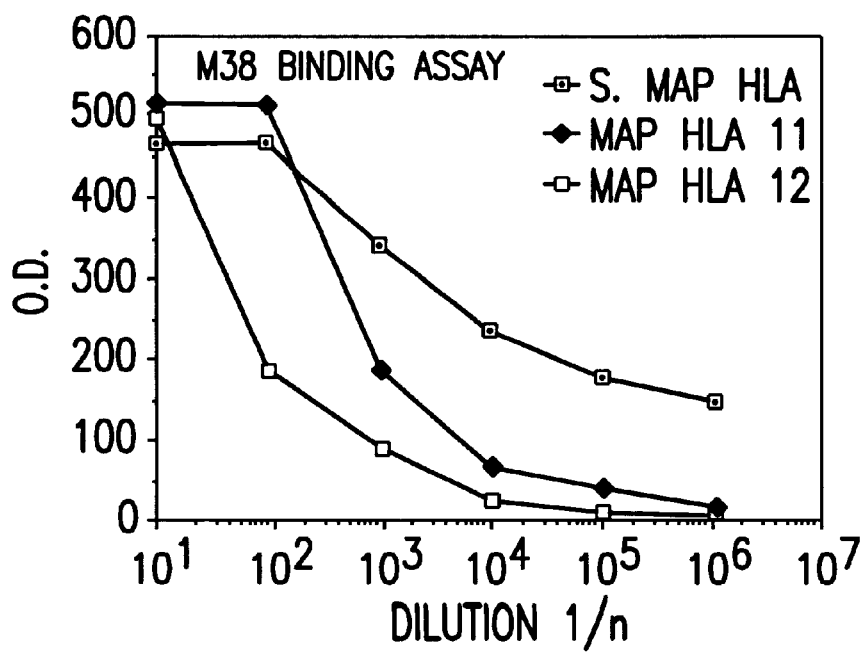
Figure 8:
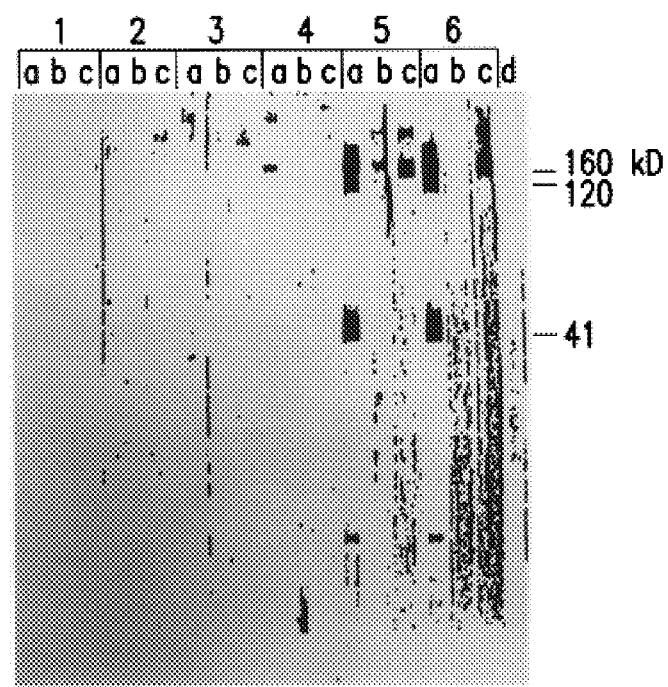
Figure 10:
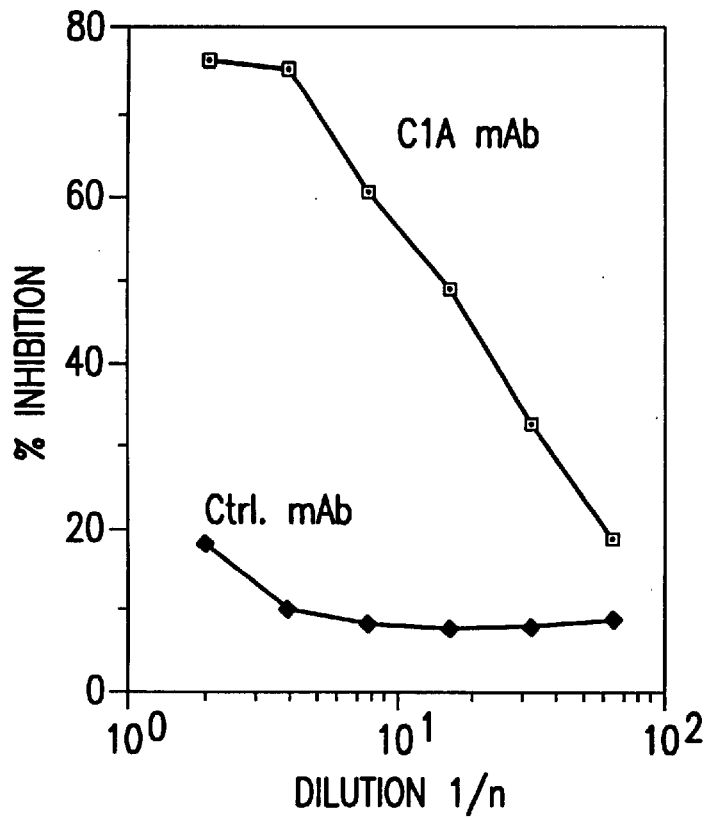
Figure 11:
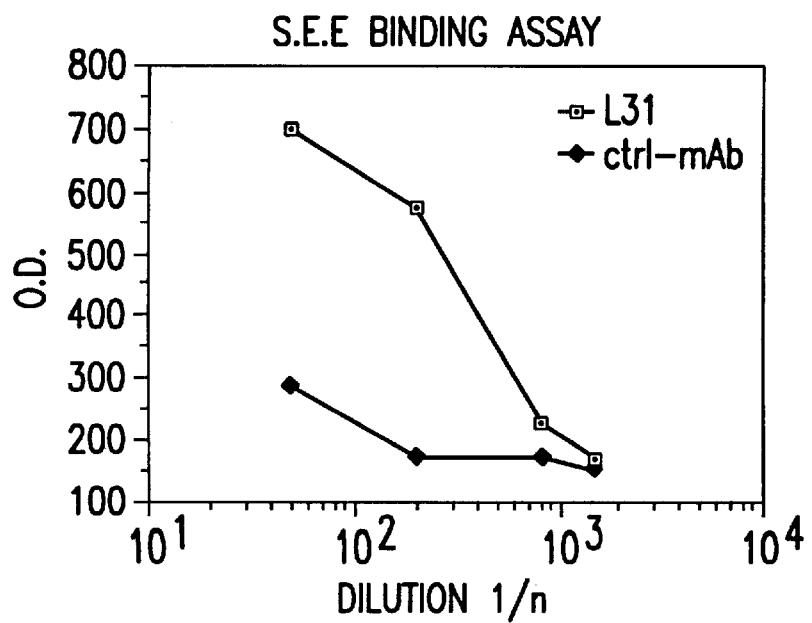

FIG. 8 shows a western blot binding assay of gp160 with sera of subjects treated with wild-type strain Vaccinia Virus (1 and 2), with recombinant gp160 (3 and 4) and with recombinant Vaccinia Virus expressing on its surface the HIV gp160 complex (5 and 6); (a) "in toto"; (b) after pre-adsorption with the S.MAP HIV peptide and elution; (c) after pre-adsorption with the S.MAP HLA peptide and elution; (d) pool of 5 and 6 sera pre-adsorbed with an unrelated peptide and eluted;

FIG. 9 shows a syncytium formation inhibition assay;

FIG. 10 shows another syncytium formation inhibition assay;

FIG. 11 shows a binding assay of the L31 antibody with the SEE protein.

EXAMPLE 1

Identification of Immunogically Homologous Regions Between gp160 and HLA and Synthetic Peptide Production The homology regions between class I HLA and HIV gp160 protein are determined by analysis of the gp160 amino acid sequence and the consensus sequence of the HLA gene locus C (Grassi et al., J. Exp. Med. 174, 53–62, 1980). Among regions showing a sinificative level of sequence homology, the COOH C-5 terminal of gp160 and the α-1 heavy chain region of HLA are selected and analyzed.

The amino acid alignment of the two regions, sequences of which are shown in the Table 1 herebelow, shows a sequence of three identical amino acids (K66, Y67 and K68 of HLA, according to the numeration of Grassi et al., "J. Exp.Med.", 174, 53–62, 1980 as well as K490, Y491 and K492 of gp160, according to the numeration of Wein-Obson et al., "Cell", 40, 9, 1985.

TABLE 1

| Peptide sequence from HV gp 160 and HLA | | |
|---|---|---|
| S. MAP HIV | SELYKYKVVKIEPLGVAPTKAKRRVV | (SEQ. ID. NO:1) |
| MAP HIV 11 | SELYKYKVVK | (SEQ. ID. NO:3) |

TABLE 1-continued

| Peptide sequence from HV gp 160 and HLA | | |
|---|---|---|
| MAP HIV 9 | IEPLGVAPT | (SEQ. ID. NO:5) |
| MAP HIV 12 | PTKAKRRVV | (SEQ. ID. NO:4) |
| S. MAP HLA | TQKYKRQAQADRVNLRKLRGYY | (SEQ. ID. NO:2) |
| MAP HLA 11 | TQKYKRQAQ | (SEQ. ID. NO:6) |
| MAP HLA 12 | NLRKLRGYY | (SEQ. ID. NO:7) |

Synthetic peptides corresponding to HLA and gp160 sequences as above are synthesized using an automatic synthesizer equipment (ABI 431/A from Applied Biosystems) and a FMOC chemistry procedure.

All of peptides are purified to homogeneity by ion-exchange chromatography followed by a reverse phase HPLC. The peptide amino acid contents comply with the expected data.

EXAMPLE 2

Antigenic Homology Among gp160 and HLA Peptides

S.MAP HIV and S. MAP HLA peptides are injected subcutaneously to BALB/c female mice together with Freund's incomplete adjuvant. After the third immunization (for a total of three immunizations at three week intervals) mice sera are tested by an ELISA assay with the recombinant gp160 protein (from Transgene, Strasbourg) as follows: microtiter plastic wells (NUNC) are coated with 0.2 $\mu$g of protein resuspended in phospahte buffer pH 9, for 1.5 hours at 37° C., followed by washing with phosphate buffer pH 7, and by further incubating for 1 hour at 37° C. with bovine serum albumin (BSA, 1 mg/ml), to saturate the free sites of solid phase. After three washings, diluted sera in PBS, comprising BSA 1% w/v, are incubated with the coated wells for 1 hour at 37° C. After five washings in PBS, a rabbit anti-mouse Igs serum (SIGMA), 1/1000 diluted, is added. After 45 min. incubation at 37° C., wells are washed five times and 100 $\mu$l of chromogen substrate is added to each well (SORIN BIOMEDICA, Saluggia, Italy). The adsorbance is read with an automatic ELISA reader (BIORAD).

Figure 1:
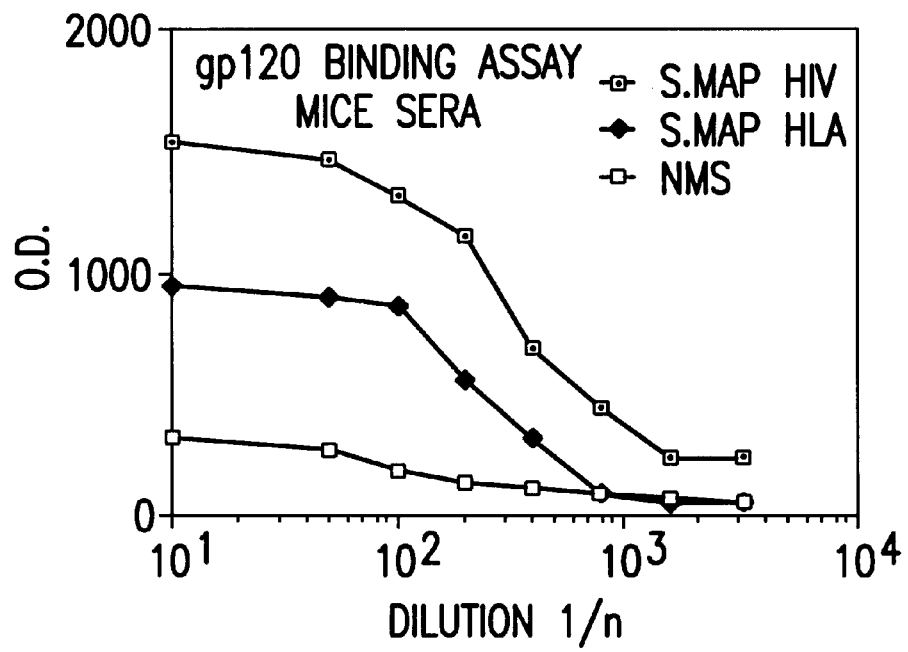
FIG. 1 shows an ELISA assay with the gp160 protein and sera obtained from mice immunized with different gp160 derived peptides.

The results are shown in FIG. 1. Sera from S. MAP HLA peptide immunized mice react specifically with the recombinant gp160 protein when compared with a mouse serum immunized with a control peptide (NMS). As expected, the sera of mice immunized with the S. MAP HIV peptide react at significantly higher level. The results show that the gp160 and the HLA regions cross-react immunologically and thus have common antigenic determinants.

The inventor already described a murine monoclonal antibody, named M38, which selectively reacts with HLA free molecules (heavy chains not associated with β-2 microglobulin) and with the HIV gp160, as well as a further monoclonal antibody, L31, which reacts with the HLA free chains, but negative when submitted to a viral gp160 western blot assay (Beretta and al., "Eur. J. Immunol.", 17, 1793–1798, 1987; Grassi and al., "J. Exp. Med.", 174, 53–62, 1980). Therefore both antibodies could be properly used to confirm the antigenic homology of the regions already identified by means of mice polyclonal sera.

Both antibodies are tested by ELISA assays with synthetic peptides of Table 1. The test conditions are those of Example 1, except that the solid phase antigen (synthetic peptide) is present at a lower concentration (0.2 μg/ml). The results of FIG. 2 show that both antibodies recognize both HLA peptide and gp160 peptide, thus confirming the antigen homology resulting from the previous tests.

EXAMPLE 3

Identification of the Common Epitopes of HLA and HIV gp160

Figure 3:
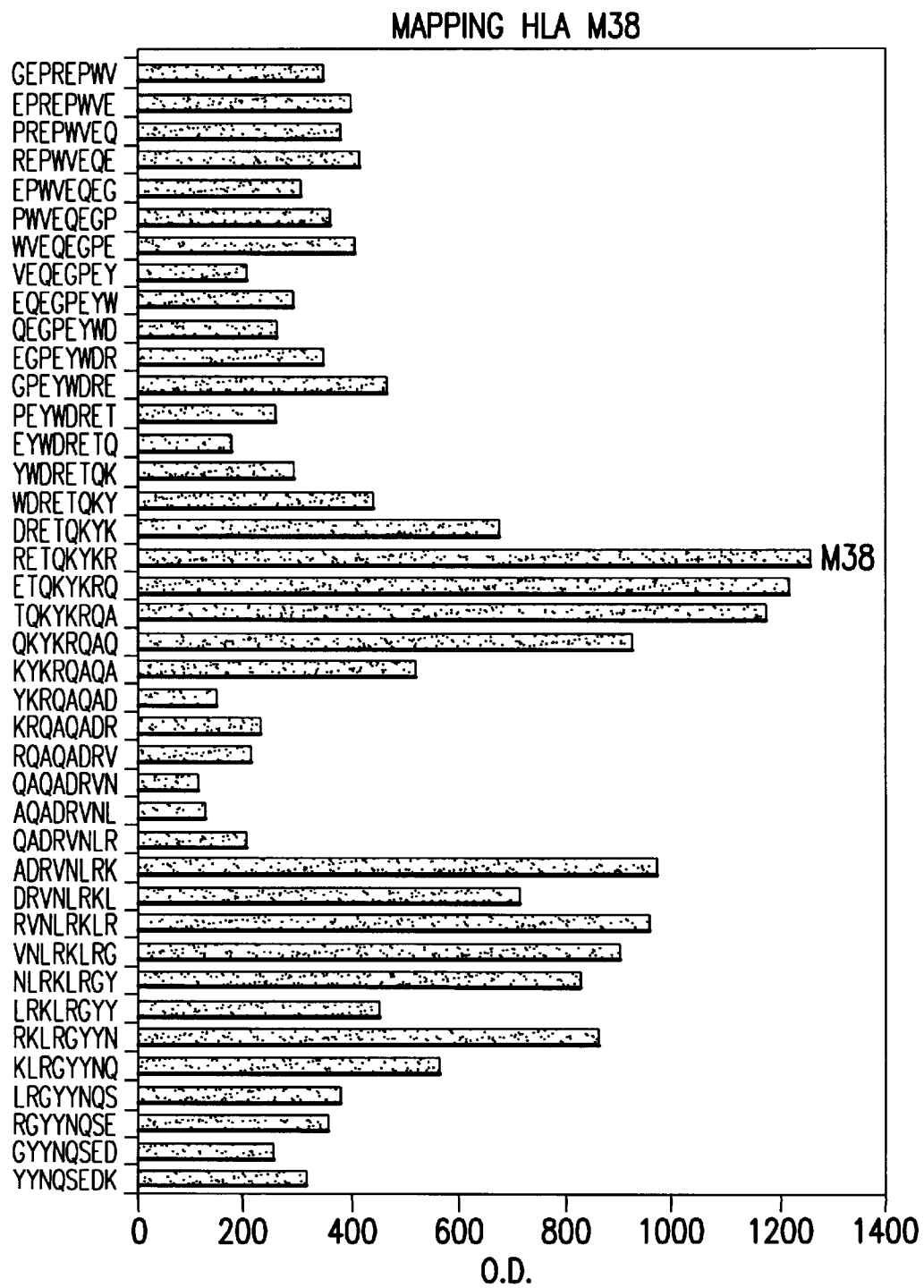
FIG. 3 is an histogram showing the M38 antibody binding to 45 one amino acid overlapping peptides, which are obtained from the HLA sequence.
Figure 4:
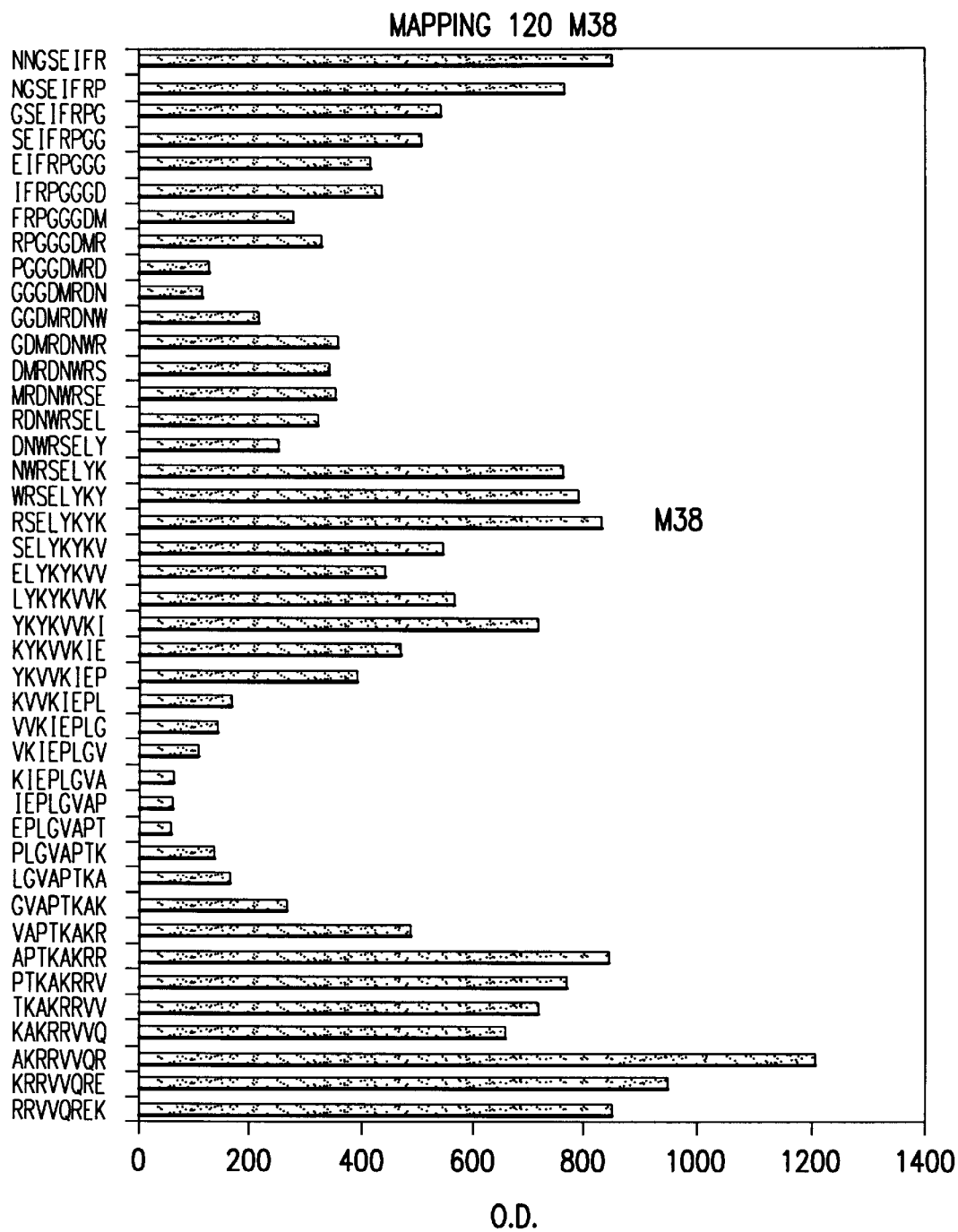
FIG. 4 is an histogram showing the M38 antibody binding to 45 one amino acid overlapping peptides, which are obtained from the gp160 sequence.

As the HLA and gp160 regions, which are defined as immunologically homologous by polyclonal sera and by L31 and M38 antibodies, extend over a long portion of both HLA and gp160 proteins, the homologous epitopes are identified by a M38 monoclonal antibody assay with two sets of 45, one amino acid overlapping, synthetic peptides, which respectively extend over the HLA and gp160 region, as shown respectively in FIG. 3 and 4.

Purposely, a synthetic peptide commercial system (CAMBRIDGE RESEARCH BIOCHEMICALS) is used directly on the solid phase. The M38 antibody is then incubated with the solid phase peptides for 12 hours at 4° C. at two different dilutions (5 and 0.5 μg/ml); the wells are washed with PBS and the M38 binding is detected by means of goat peroxidase-conjugated anti-rat Igs serum (SIGMA) at 1/1000 dilution in PBS with 0.5% w/v BSA. The colorimetric reaction, detected by the chromogen substrate (OPD/$H_2O_2$) is directly proportional to the antibody amount bound to the solid phase.

The test results, as showed in the FIGS. 3 and 4, indicate that the M38 antibody recognize two different epitopes on both molecules; namely, M38 defines a first epitope, corresponding to the K66, Y67 and K68 residues and a second epitope, corresponding to L78, R79, K80, L81 and R82 residues, according to the above mentioned numeration, for HLA. For gp160, the two epitopes are respectively K490, Y491, K492 and K505; A506, K507, R508 and R509 (KAKRR; SEQ ID NO:90), according to the above mentioned numeration.

An amino acid motif, common to the four epitopes, is a first lysine, followed by a hydrophobic residue and a second lysine or an arginine. The two epitopes are separated on both molecules by an intervening sequence with a comparable amount of residues (12 on gp160 and 9 on HLA), thus showing a strong structural homology between both proteins.

On the basis of known cristallography data (Bjorkman and al., "Nature", 329, 506, 1987), both HLA epitopes correspond to the HLA hypervariable region, as they comprise at least one polymorphic site, that results to be oriented to the inner part of the native molecule and is involved in the binding of peptide fragments of HLA-carrying antigens.

EXAMPLE 4

Detection of an Autoimmunity Response in AIDS Affected Patients

An assay for the induction of auto-immunity response during the disease progression is carried out.

Figure 5:
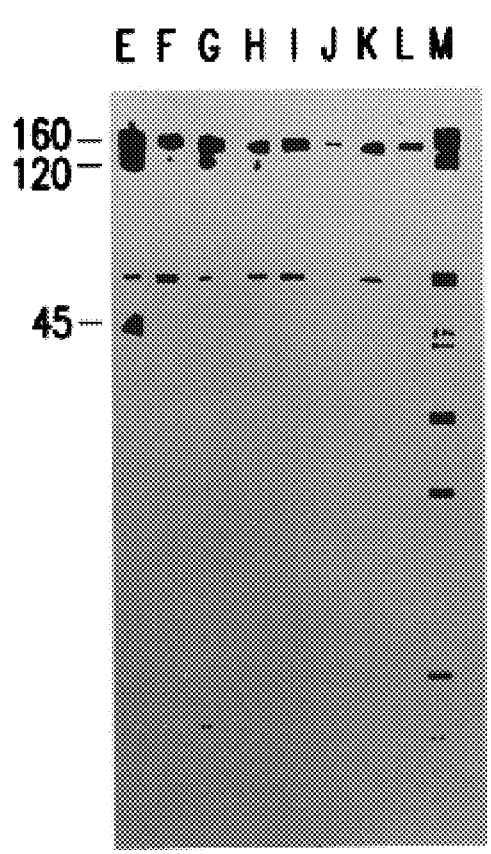
FIG. 5 shows a western blot binding assay of gp160 with sera from AIDS patients, pre-immunoadsorbed with S. MAP HLA, MAP HLA 11 or MAP HLA 12 peptides and eluted.

Sera from AIDS affected subjects are immunoadsorbed on columns of either S. MAP HIV, or MAP HLA 11 or MAP HLA 12 peptide coupled Sepharose (CNBR activated sepharose 4B from PHARMACIA) and eluted. 1 ml of Sepharose/peptide equilibrated with 0.1 M TRIS HCl pH 8 and 0.5 M NaCl buffer is incubated for 16 hours with 100 μl of serum, washed with 0.1 M TRIS HCl ph 8 and 0.5 M NaCl. The bound antibodies are eluted with a buffer containing 0.2 M glycine pH 2 and 0.5 M NaCl. The eluted antibodies are assayed on HIV western blot commercial stripes (SORIN BIOMEDICA, Saluggia, Italy) and detected using the chemio-luminescence system from AMERSHAM. The results are shown in FIG. 5, showing a HIV western blot of purified antibodies by two different sera with the MAP HLA 12 peptide (lanes E and I), the MAP HLA 11 peptide (lanes F and J), both peptides mixed in equimolar amount (lanes G and K), and S. MAP HIV peptide (lanes H and L). Lane M is obtained from one of the "in toto" sera and used as control. The data show that either HLA or HIV peptide pre-adsorbed antibodies bind similarly to the viral gp160. In one case (lane E), the antibodies also bind to a 45 KD protein, which is likely corresponding to HLA heavy chains. Therefore, it can be stated that anti-gp160 antibodies cross-react with HLA.

Figure 6:
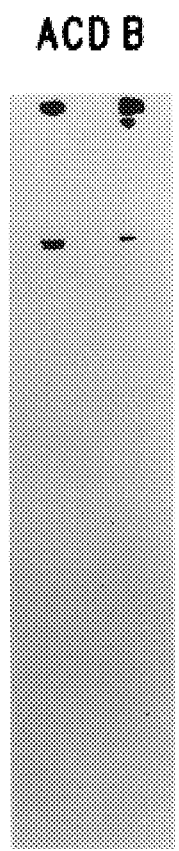
FIG. 6 shows a western blot binding assay of gp160 with sera from AIDS patients, pre-immunoadsorbed with S. MAP HLA, or MAP HIV 9 peptides and eluted.

The same test is carried out using two sera of AIDS affected patients (FIG. 6), pre-adsorbed with the S. MAP HIV peptide (lanes A and B) or with the HIV 9 peptide (lanes C and D), and eluted. The last ones do not show any reactivity, thus showing that antibodies raised against the native gp160 protein, react with the HIV 11 and HIV 12 regions, and not with the HIV 9 regions.

EXAMPLE 5

Detection of an Auto-immune Response in gp160 Vaccinated Subjects

The same test method is applied using sera of serum-negative vaccinated patients.

Figure 7:
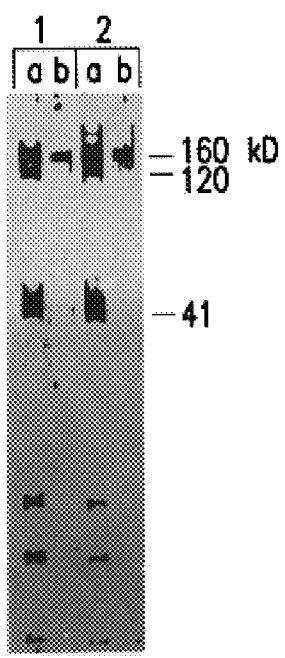
FIG. 7 shows a western blot binding assay of gp160 with sera from two subjects (1 and 2) vaccinated with both Vaccinia Virus and the gp160 recombinant protein; (a) "in toto", and (b) after pre-adsorption with the S.MAP HLA peptide and elution.

FIG. 7 shows a gp160 binding assay of sera of two subjects which are vaccinated with Vaccinia Virus (from Bristol-Myers), as well as with the gp160 recombinant protein (from VanSyn Microgenesis) (lanes 1 and 2): (a) "in toto"; (b) after pre-absorption with the S. MAP HLA peptide. FIG. 8 shows a gp160 binding assay of sera of subjects vaccinated with Vaccinia Virus (lanes 1 and 2), recombinant gp160 (lanes 3 and 4), recombinant HIV gp160 surface expressing Vaccinia Virus, followed by a gp160 recombinant boost (HIVAC, Bristol-Myers),(lanes 5 and 6): (a) "in toto"; (b) after pre-absorption with the S.MAP HIV peptide and elution; (c) after pre-absorption with the S.MAP HLA peptide and elution; (d) pool of two pre-adsorbed sera with a un correlated peptide.

These data show a positive relationship between the ability of a gp160 vaccine to induce a significant serological response and an anti-HLA response.

EXAMPLE 6

Neutralizing Activity of Anti-S. MAP HLA Peptide Antibodies

In order to check the ability to neutralize the viral infection of sera raised against the HLA homologous regions, mice sera are prepared by immunization with either S. MAP HLA or S. MAP HIV peptides. Sera are assayed for antibody ability to inhibit syncytium cells between HIV infected cells (8E51 LAV cells, AIDS Repository National Insitute of Health, Bethesda, Md. USA, "Journ. Exp. Medicine, 164, 280, 1986) and not infected, CD4+cells (MOLT3 cells, AIDS Repository National Institute of Health, Bethesda, Md., USA). The syncytiums are counted at the optical microscope and the inhibition percentages are evaluated with reference to syncytiums in a control antibody-free cell culture. As specifity control, sera of mice before immunization are used. The results (FIG. 9) show that antibodies against the HLA peptide (S.MAP HLA) comprising gp160 homologous regions has the same ability to neutralize the viral fusion than antibodies against the gp160 homologous peptide (S. MAP HIV).

Accordingly, there is a positive correlation between the anti-HLA cross-reactive response and the viral infection neutralizing response.

EXAMPLE 7

Neutralizing Activity of Anti-HIV 9 Peptide Antibodies

Experiments published by Helseth and coworkers in 1991 (Journ of Virol. 65, 2119–2123, 1991 ) show that 5 of the 9 residues of the peptide HIV-9 of gp160 (peptide IEPLGVAPT) (SEQ ID NO:5) are essential to the maintainance of the quaternary structure of the envelope since single amino acid substitutions within these positions result in a high dissociation rate between gp160 and gp41. As reported in Example 4 none of sera from HIV positive subjects are reactive with the HIV-9 peptide, whereas all of them are reactive with the two flanking regions bearing the HLA homologous epitopes.

In order to investigate whether the presence of the two HLA homologous epitopes flanking the IEPLGVAPT (SEQ. ID. NO:5) sequence influence negatively the antibody response against this region and prevent the production of antibodies against a potentially neutralizable site, BALB/c mice are immunized with the IEPLGVAPT (SEQ. ID. NO:5) peptide and complete Freund's agjuvant. After four antigen boosts, spleen cells of sacrified mice are fused with the myeloma cell line NS1, to generate a number of hybridomas. All hybridomas are screened by ELISA with the IEPLGVAPT (SEQ. ID. NO:5) peptide. One hybridoma (C1A) is selected for its reactivity against the IEPLGVAPT (SEQ ID. NO:5) peptide and tested for inhibition of HIV induced cell fusion using the syncitia assay described in Example 6. Briefly, 8E51 LAV cells (AIDS Repository National Institute of Health, Bethesda, Md., USA, Journ. Exp. Medicine 164, 280, 1986) and CD4+MOLT3 cells (AIDS Repository National Institute of Health, Bethesda, Md., USA) are mixed in V shaped wells, incubated for three hours and syncitia counted at the microscope. As it can be seen in FIG. 9, the C1A antibody inhibits syncitia formation in a dose dependent manner. Thus the IEPLGVAPT (SEQ. ID. No:5) sequence is a neutralizable site of the HIV envelope necessary to HIV induced cell fusion which is non immunogenic in HIV infected individuals. Antibodies to this sequence may have protective effects against HIV infection.

EXAMPLE 8

Immunological Homolgy of Both HLA and gp160 Epitopes With a Bacterial Superantigen Some recent experiments (Imberti et al. "Science", 254, 869, 1991) suggest that, in the course of the HIV infection, the T lymphocyte population of the patient suffers. functional alterations, that are similar to alterations which are observed with test animals, as well with human lymphocytes in vitro when exposed to superantigenic substances. Such modifications essentially consist of a selective loss of some T receptors, which express some genes of the family of the variable β-region. Superantigens are defined as bacterial glycoproteins being able to bind the β-chains of the T lymphocyte receptor ando to the class 2 HLA molecules (Marrack and Kappler, Science", 248, 705, 1990), thus activating the target cell and inducing the cell death for apoctosys. Some Vβ families are eliminated by the T lymphocyte population during-the HIV infection, thus suggesting an HIV superantigenic effect. In order to verify whether gp160 HLA homologous epitopes have also superantigenic features, as being able to bind the T lymphocyte receptor, an ELISA assay is carried out, under the same conditions as in Example 1, using the L31 antibody, which showed to be specific to define the HLA/gp160 homology in the previous experiments, with a known superantigen, the SEE protein (from SERVIA BIOCHEMIA, Germany).

As shown in FIG. 10, the test demonstrates that the HIV homologous HLA regions are able to induce anti-HLA auto-antibodies, and act as superantigens during the infection course, leading to a gradual and selective loss of certain T receptor families.

I claim:

1. An isolated peptide having the amino acid sequence SELYKYKVVK (SEQ ID NO:3).

2. An isolated peptide having the amino acid sequence PTKAKRRVV (SEQ ID NO:4).

3. An isolated peptide having an amino acid sequence selected from the group consisting of SELYKYKV (SEQ ID NO:27), ELYKYKVV (SEQ ID NO:28), LYKYKVVK (SEQ ID NO:29), and YKYKVVKI (SEQ ID NO:30).

4. An immunogenic composition comprising the peptide of any one of claims 1, 2 or 3 and a carrier.

5. An isolated peptide having an amino acid sequence selected from the group consisting of KYKVVKIE (SEQ ID NO:31), VAPTKAKR (SEQ ID NO:42), APTKAKRR (SEQ ID NO:43), PTKAKRRV (SEQ ID NO:44), TKAKRRVV (SEQ. ID NO:45), KAKRRVVQ (SEQ ID NO:46), AKRRVQR (SEQ ID NO:47), KRRVVQRE (SEQ ID NO:48) and RRVVQREK (SEQ ID NO:49).

6. A composition comprising the peptide of claim 5 and a carrier.

7. A method of inducing an immune response to the human immunodeficiency virus protein gp160 in a subject comprising administering, to the subject, an effective amount of a peptide according to any one of claims 1, 2, 3 and 6.

8. An isolated peptidic subfragment of the human immunodeficiency virus (HIV) gp160 envelope glycoprotein, wherein said subfragment is obtained from a gp160 fragment defined by the contiguous overlapping peptides having SEQ ID NOS.: 8–49, said subfragment further comprising a first and second epitope, wherein said first epitope has the amino acids K490, Y491, and K492 and said second epitope has the amino acids K505, A506, K507, R508, and R509.

* * * * *

SEQUENCE LISTING (1) GENERAL INFORMATION:

(iii) NUMBER OF SEQUENCES: 90

(2) INFORMATION FOR SEQ ID NO:1:

(i) SEQUENCE CHARACTERISTICS:
      (A) LENGTH: 26 amino acids
      (B) TYPE: amino acid
      (C) STRANDEDNESS:
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:1:

Ser Glu Leu Tyr Lys Tyr Lys Val Val Lys Ile Glu Pro Leu Gly Val
1               5                   10                  15

Ala Pro Thr Lys Ala Lys Arg Arg Val Val
            20                  25

(2) INFORMATION FOR SEQ ID NO:2:

(i) SEQUENCE CHARACTERISTICS:
            (A) LENGTH: 22 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:2:

Thr Gln Lys Tyr Lys Arg Gln Ala Gln Ala Asp Arg Val Asn Leu Arg
1               5                   10                  15

Lys Leu Arg Gly Tyr Tyr
            20

(2) INFORMATION FOR SEQ ID NO:3:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:3:

Ser Glu Leu Tyr Lys Tyr Lys Val Val Lys
1               5                   10

(2) INFORMATION FOR SEQ ID NO:4:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal

```
        (vi) ORIGINAL SOURCE:

(xi) SEQUENCE DESCRIPTION: SEQ ID NO:4:

Pro Thr Lys Ala Lys Arg Arg Val Val
1               5

(2) INFORMATION FOR SEQ ID NO:5:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:5:

Ile Glu Pro Leu Gly Val Ala Pro Thr
1               5

(2) INFORMATION FOR SEQ ID NO:6:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

Thr Gln Lys Tyr Lys Arg Gln Ala Gln
1               5

(2) INFORMATION FOR SEQ ID NO:7:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:7:

Asn Leu Arg Lys Leu Arg Gly Tyr Tyr
1               5
```

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:8:

Asn Asn Gly Ser Glu Ile Phe Arg
1               5

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:9:

Asn Gly Ser Glu Ile Phe Arg Pro
1               5

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:10:

Gly Ser Glu Ile Phe Arg Pro Gly
1               5

(2) INFORMATION FOR SEQ ID NO:11:

(i) SEQUENCE CHARACTERISTICS:
        (A) LENGTH: 8 amino acids
        (B) TYPE: amino acid (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:11:

Ser Glu Ile Phe Arg Pro Gly Gly
 1               5

(2) INFORMATION FOR SEQ ID NO:12:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:12:

Glu Ile Phe Arg Pro Gly Gly Gly
 1               5

(2) INFORMATION FOR SEQ ID NO:13:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:13:

Ile Phe Arg Pro Gly Gly Gly Asp
 1               5

(2) INFORMATION FOR SEQ ID NO:14:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:14:

Phe Arg Pro Gly Gly Gly Asp Met
  1               5

(2) INFORMATION FOR SEQ ID NO:15:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:15:

Arg Pro Gly Gly Gly Asp Met Arg
  1               5

(2) INFORMATION FOR SEQ ID NO:16:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:16:

Pro Gly Gly Gly Asp Met Arg Asp
  1               5

(2) INFORMATION FOR SEQ ID NO:17:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:17:

```
Gly Gly Gly Asp Met Arg Asp Asn
1               5
```

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:18:

```
Gly Gly Asp Met Arg Asp Asn Trp
1               5
```

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:19:

```
Gly Asp Met Arg Asp Asn Trp Arg
1               5
```

(2) INFORMATION FOR SEQ ID NO:20:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:20:

```
Asp Met Arg Asp Asn Trp Arg Ser
1               5
```

(2) INFORMATION FOR SEQ ID NO:21:

```
    (i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:21:

Met Arg Asp Asn Trp Arg Ser Glu
1               5

(2) INFORMATION FOR SEQ ID NO:22:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:22:

Arg Asp Asn Trp Arg Ser Glu Leu
1               5

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:23:

Asp Asn Trp Arg Ser Glu Leu Tyr
1               5

(2) INFORMATION FOR SEQ ID NO:24:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide
```

```
        (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:24:

Asn Trp Arg Ser Glu Leu Tyr Lys
 1               5

(2) INFORMATION FOR SEQ ID NO:25:

(i) SEQUENCE CHARACTERISTICS:
              (A) LENGTH: 8 amino acids
              (B) TYPE: amino acid
              (C) STRANDEDNESS:
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:25:

Trp Arg Ser Glu Leu Tyr Lys Tyr
 1               5

(2) INFORMATION FOR SEQ ID NO:26:

(i) SEQUENCE CHARACTERISTICS:
              (A) LENGTH: 8 amino acids
              (B) TYPE: amino acid
              (C) STRANDEDNESS:
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:26:

Arg Ser Glu Leu Tyr Lys Tyr Lys
 1               5

(2) INFORMATION FOR SEQ ID NO:27:

(i) SEQUENCE CHARACTERISTICS:
              (A) LENGTH: 8 amino acids
              (B) TYPE: amino acid
              (C) STRANDEDNESS:
              (D) TOPOLOGY: linear (ii) MOLECULE TYPE: peptide (iii) HYPOTHETICAL: NO (iv) ANTI-SENSE: NO (v) FRAGMENT TYPE: internal
```

(vi) ORIGINAL SOURCE:

(xi) SEQUENCE DESCRIPTION: SEQ ID NO:27:

Ser Glu Leu Tyr Lys Tyr Lys Val
 1               5

(2) INFORMATION FOR SEQ ID NO:28:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:28:

Glu Leu Tyr Lys Tyr Lys Val Val
 1               5

(2) INFORMATION FOR SEQ ID NO:29:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:29:

Leu Tyr Lys Tyr Lys Val Val Lys
 1               5

(2) INFORMATION FOR SEQ ID NO:30:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:30:

Tyr Lys Tyr Lys Val Val Lys Ile
 1               5

(2) INFORMATION FOR SEQ ID NO:31:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:31:

Lys Tyr Lys Val Val Lys Ile Glu
 1               5

(2) INFORMATION FOR SEQ ID NO:32:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:32:

Tyr Lys Val Val Lys Ile Glu Pro
 1               5

(2) INFORMATION FOR SEQ ID NO:33:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:33:

Lys Val Val Lys Ile Glu Pro Leu
 1               5

(2) INFORMATION FOR SEQ ID NO:34:

(i) SEQUENCE CHARACTERISTICS:
         (A) LENGTH: 8 amino acids
         (B) TYPE: amino acid
         (C) STRANDEDNESS:

```
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:34:

Val Val Lys Ile Glu Pro Leu Gly
  1               5

(2) INFORMATION FOR SEQ ID NO:35:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:35:

Val Lys Ile Glu Pro Leu Gly Val
  1               5

(2) INFORMATION FOR SEQ ID NO:36:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:36:

Lys Ile Glu Pro Leu Gly Val Ala
  1               5

(2) INFORMATION FOR SEQ ID NO:37:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO
```

```
        (v) FRAGMENT TYPE: internal (vi) ORIGINAL SOURCE:

(xi) SEQUENCE DESCRIPTION: SEQ ID NO:37:

Ile Glu Pro Leu Gly Val Ala Pro
 1               5

(2) INFORMATION FOR SEQ ID NO:38:

(i) SEQUENCE CHARACTERISTICS:
             (A) LENGTH: 8 amino acids
             (B) TYPE: amino acid
             (C) STRANDEDNESS:
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:38:

Glu Pro Leu Gly Val Ala Pro Thr
 1               5

(2) INFORMATION FOR SEQ ID NO:39:

(i) SEQUENCE CHARACTERISTICS:
             (A) LENGTH: 8 amino acids
             (B) TYPE: amino acid
             (C) STRANDEDNESS:
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:39:

Pro Leu Gly Val Ala Pro Thr Lys
 1               5

(2) INFORMATION FOR SEQ ID NO:40:

(i) SEQUENCE CHARACTERISTICS:
             (A) LENGTH: 8 amino acids
             (B) TYPE: amino acid
             (C) STRANDEDNESS:
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:40:
```

```
Leu Gly Val Ala Pro Thr Lys Ala
1               5
```

(2) INFORMATION FOR SEQ ID NO:41:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:41:

```
Gly Val Ala Pro Thr Lys Ala Lys
1               5
```

(2) INFORMATION FOR SEQ ID NO:42:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:42:

```
Val Ala Pro Thr Lys Ala Lys Arg
1               5
```

(2) INFORMATION FOR SEQ ID NO:43:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:43:

```
Ala Pro Thr Lys Ala Lys Arg Arg
1               5
```

(2) INFORMATION FOR SEQ ID NO:44:

(i) SEQUENCE CHARACTERISTICS:

(A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:44:

Pro Thr Lys Ala Lys Arg Arg Val
1               5

(2) INFORMATION FOR SEQ ID NO:45:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:45:

Thr Lys Ala Lys Arg Arg Val Val
1               5

(2) INFORMATION FOR SEQ ID NO:46:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:46:

Lys Ala Lys Arg Arg Val Val Gln
1               5

(2) INFORMATION FOR SEQ ID NO:47:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide

```
       (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:47:

Ala Lys Arg Arg Val Val Gln Arg
1               5

(2) INFORMATION FOR SEQ ID NO:48:

(i) SEQUENCE CHARACTERISTICS:
              (A) LENGTH: 8 amino acids
              (B) TYPE: amino acid
              (C) STRANDEDNESS:
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:48:

Lys Arg Arg Val Val Gln Arg Glu
1               5

(2) INFORMATION FOR SEQ ID NO:49:

(i) SEQUENCE CHARACTERISTICS:
              (A) LENGTH: 8 amino acids
              (B) TYPE: amino acid
              (C) STRANDEDNESS:
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:49:

Arg Arg Val Val Gln Arg Glu Lys
1               5

(2) INFORMATION FOR SEQ ID NO:50:

(i) SEQUENCE CHARACTERISTICS:
              (A) LENGTH: 8 amino acids
              (B) TYPE: amino acid
              (C) STRANDEDNESS:
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
```

```
        (xi) SEQUENCE DESCRIPTION: SEQ ID NO:50:

Gly Glu Pro Arg Glu Pro Trp Val
  1               5

(2) INFORMATION FOR SEQ ID NO:51:

(i) SEQUENCE CHARACTERISTICS:
           (A) LENGTH: 8 amino acids
           (B) TYPE: amino acid
           (C) STRANDEDNESS:
           (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:51:

Glu Pro Arg Glu Pro Trp Val Glu
  1               5

(2) INFORMATION FOR SEQ ID NO:52:

(i) SEQUENCE CHARACTERISTICS:
           (A) LENGTH: 8 amino acids
           (B) TYPE: amino acid
           (C) STRANDEDNESS:
           (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:52:

Pro Arg Glu Pro Trp Val Glu Gln
  1               5

(2) INFORMATION FOR SEQ ID NO:53:

(i) SEQUENCE CHARACTERISTICS:
           (A) LENGTH: 8 amino acids
           (B) TYPE: amino acid
           (C) STRANDEDNESS:
           (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:53:

Arg Glu Pro Trp Val Glu Gln Glu
  1               5
```

(2) INFORMATION FOR SEQ ID NO:54:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:54:

Glu Pro Trp Val Glu Gln Glu Gly
 1            5

(2) INFORMATION FOR SEQ ID NO:55:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:55:

Pro Trp Val Glu Gln Glu Gly Pro
 1            5

(2) INFORMATION FOR SEQ ID NO:56:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:56:

Trp Val Glu Gln Glu Gly Pro Glu
 1            5

(2) INFORMATION FOR SEQ ID NO:57:

(i) SEQUENCE CHARACTERISTICS:
        (A) LENGTH: 8 amino acids
        (B) TYPE: amino acid
        (C) STRANDEDNESS:
        (D) TOPOLOGY: linear

```
        (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:57:

Val Glu Gln Glu Gly Pro Glu Tyr
  1               5

(2) INFORMATION FOR SEQ ID NO:58:

(i) SEQUENCE CHARACTERISTICS:
             (A) LENGTH: 8 amino acids
             (B) TYPE: amino acid
             (C) STRANDEDNESS:
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:58:

Glu Gln Glu Gly Pro Glu Tyr Trp
  1               5

(2) INFORMATION FOR SEQ ID NO:59:

(i) SEQUENCE CHARACTERISTICS:
             (A) LENGTH: 8 amino acids
             (B) TYPE: amino acid
             (C) STRANDEDNESS:
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:59:

Gln Glu Gly Pro Glu Tyr Trp Asp
  1               5

(2) INFORMATION FOR SEQ ID NO:60:

(i) SEQUENCE CHARACTERISTICS:
             (A) LENGTH: 8 amino acids
             (B) TYPE: amino acid
             (C) STRANDEDNESS:
             (D) TOPOLOGY: linear (ii) MOLECULE TYPE: peptide (iii) HYPOTHETICAL: NO (iv) ANTI-SENSE: NO
```

(v) FRAGMENT TYPE: internal (vi) ORIGINAL SOURCE:

(xi) SEQUENCE DESCRIPTION: SEQ ID NO:60:

Glu Gly Pro Glu Tyr Trp Asp Arg
1               5

(2) INFORMATION FOR SEQ ID NO:61:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:61:

Gly Pro Glu Tyr Trp Asp Arg Glu
1               5

(2) INFORMATION FOR SEQ ID NO:62:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:62:

Pro Glu Tyr Trp Asp Arg Glu Thr
1               5

(2) INFORMATION FOR SEQ ID NO:63:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:63:

Glu Tyr Trp Asp Arg Glu Thr Gln

```
              1               5

(2) INFORMATION FOR SEQ ID NO:64:

(i) SEQUENCE CHARACTERISTICS:
          (A) LENGTH: 8 amino acids
          (B) TYPE: amino acid
          (C) STRANDEDNESS:
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:64:

Tyr Trp Asp Arg Glu Thr Gln Lys
  1               5

(2) INFORMATION FOR SEQ ID NO:65:

(i) SEQUENCE CHARACTERISTICS:
          (A) LENGTH: 8 amino acids
          (B) TYPE: amino acid
          (C) STRANDEDNESS:
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:65:

Trp Asp Arg Glu Thr Gln Lys Tyr
  1               5

(2) INFORMATION FOR SEQ ID NO:66:

(i) SEQUENCE CHARACTERISTICS:
          (A) LENGTH: 8 amino acids
          (B) TYPE: amino acid
          (C) STRANDEDNESS:
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:66:

Asp Arg Glu Thr Gln Lys Tyr Lys
  1               5

(2) INFORMATION FOR SEQ ID NO:67:

(i) SEQUENCE CHARACTERISTICS:
          (A) LENGTH: 8 amino acids
```

-continued

```
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:67:

Arg Glu Thr Gln Lys Tyr Lys Arg
1               5

(2) INFORMATION FOR SEQ ID NO:68:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:68:

Glu Thr Gln Lys Tyr Lys Arg Gln
1               5

(2) INFORMATION FOR SEQ ID NO:69:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:69:

Thr Gln Lys Tyr Lys Arg Gln Ala
1               5

(2) INFORMATION FOR SEQ ID NO:70:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO
```

(iv) ANTI-SENSE: NO (v) FRAGMENT TYPE: internal (vi) ORIGINAL SOURCE:

(xi) SEQUENCE DESCRIPTION: SEQ ID NO:70:

Gln Lys Tyr Lys Arg Gln Ala Gln
 1               5

(2) INFORMATION FOR SEQ ID NO:71:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:71:

Lys Tyr Lys Arg Gln Ala Gln Ala
 1               5

(2) INFORMATION FOR SEQ ID NO:72:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:72:

Tyr Lys Arg Gln Ala Gln Ala Asp
 1               5

(2) INFORMATION FOR SEQ ID NO:73:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:73:

Lys Arg Gln Ala Gln Ala Asp Arg
1               5

(2) INFORMATION FOR SEQ ID NO:74:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:74:

Arg Gln Ala Gln Ala Asp Arg Val
1               5

(2) INFORMATION FOR SEQ ID NO:75:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:75:

Gln Ala Gln Ala Asp Arg Val Asn
1               5

(2) INFORMATION FOR SEQ ID NO:76:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:76:

Ala Gln Ala Asp Arg Val Asn Leu
1               5

(2) INFORMATION FOR SEQ ID NO:77:

```
    (i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:77:

Gln Ala Asp Arg Val Asn Leu Arg
 1               5

(2) INFORMATION FOR SEQ ID NO:78:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:78:

Ala Asp Arg Val Asn Leu Arg Lys
 1               5

(2) INFORMATION FOR SEQ ID NO:79:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:79:

Asp Arg Val Asn Leu Arg Lys Leu
 1               5

(2) INFORMATION FOR SEQ ID NO:80:

(i) SEQUENCE CHARACTERISTICS:
        (A) LENGTH: 8 amino acids
        (B) TYPE: amino acid
        (C) STRANDEDNESS:
        (D) TOPOLOGY: linear
```

(ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:80:

Arg Val Asn Leu Arg Lys Leu Arg
  1               5

(2) INFORMATION FOR SEQ ID NO:81:

(i) SEQUENCE CHARACTERISTICS:
             (A) LENGTH: 8 amino acids
             (B) TYPE: amino acid
             (C) STRANDEDNESS:
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:81:

Val Asn Leu Arg Lys Leu Arg Gly
  1               5

(2) INFORMATION FOR SEQ ID NO:82:

(i) SEQUENCE CHARACTERISTICS:
             (A) LENGTH: 8 amino acids
             (B) TYPE: amino acid
             (C) STRANDEDNESS:
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:82:

Asn Leu Arg Lys Leu Arg Gly Tyr
  1               5

(2) INFORMATION FOR SEQ ID NO:83:

(i) SEQUENCE CHARACTERISTICS:
             (A) LENGTH: 8 amino acids
             (B) TYPE: amino acid
             (C) STRANDEDNESS:
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:83:

Leu Arg Lys Leu Arg Gly Tyr Tyr
 1               5

(2) INFORMATION FOR SEQ ID NO:84:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:84:

Arg Lys Leu Arg Gly Tyr Tyr Asn
 1               5

(2) INFORMATION FOR SEQ ID NO:85:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:85:

Lys Leu Arg Gly Tyr Tyr Asn Gln
 1               5

(2) INFORMATION FOR SEQ ID NO:86:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:86:

Leu Arg Gly Tyr Tyr Asn Gln Ser
 1               5

(2) INFORMATION FOR SEQ ID NO:87:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:87:

Arg Gly Tyr Tyr Asn Gln Ser Glu
 1               5

(2) INFORMATION FOR SEQ ID NO:88:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:88:

Gly Tyr Tyr Asn Gln Ser Glu Asp
 1               5

(2) INFORMATION FOR SEQ ID NO:89:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:89:

Tyr Tyr Asn Gln Ser Glu Asp Lys
 1               5

(2) INFORMATION FOR SEQ ID NO:90:

(i) SEQUENCE CHARACTERISTICS:
        (A) LENGTH: 5 amino acids
        (B) TYPE: amino acid

```
      (C) STRANDEDNESS:
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:90:

Lys Ala Lys Arg Arg
 1               5
```